United States Patent [19]

Lafon

[11] Patent Number: 4,861,801
[45] Date of Patent: Aug. 29, 1989

[54] TREATMENT OF DEPRESSION BY USING A FLUOROPHENACYLAMINE DERIVATIVE

[75] Inventor: Louis Lafon, Paris, France

[73] Assignee: Laboratoire L. Lafon, France

[21] Appl. No.: 321,356

[22] Filed: Mar. 10, 1989

Related U.S. Application Data

[63] Continuation-in-part of Ser. No. 68,702, Jul. 1, 1987, Pat. No. 4,835,315, which is a continuation of Ser. No. 867,409, May 14, 1986, abandoned, which is a continuation-in-part of Ser. No. 443,934, Nov. 23, 1982, abandoned, which is a continuation of Ser. No. 252,506, Apr. 8, 1981, abandoned.

[30] Foreign Application Priority Data

Mar. 23, 1981 [FR] France ................... 81 05771

[51] Int. Cl.$^4$ ............... A61K 31/135; A61K 31/205
[52] U.S. Cl. ........................... 514/653; 514/574
[58] Field of Search .......................... 514/653, 574

[56] References Cited

U.S. PATENT DOCUMENTS 4,835,315  5/1989  Lafon ........................... 564/363

Primary Examiner—Robert V. Hines
Attorney, Agent, or Firm—Eric P. Schellin

[57] ABSTRACT

The present invention relates to a process for the treatment of depression comprising administering to a human in need thereof an antidepressant amount of a compound selected from 1-(2-fluorophenyl)-2-tertiobutylamino-1-ethanol and an addition salt thereof.

2 Claims, No Drawings

TREATMENT OF DEPRESSION BY USING A FLUOROPHENACYLAMINE DERIVATIVE

This application is a continuation-in-part of prior application Serial No. 068,702 filed on July 1, 1987 and now U.S. Pat. No. 4,835,315; which was a continuation of prior application Ser. No. 867,409 filed on May 14, 1986, and now abandoned which was a continuation-in-part of prior application Ser. No. 443,934 filed on Nov. 23, 1982, and now abandoned which in turn was a continuation of prior application Ser. No. 252,506, filed on April 8, 1981 and now abandoned.

BACKGROUND

The present invention relates, by way of new industrial products, to fluorophenacyl-amine derivatives, and also to the application thereof in therapeutics as unexpectedly and significantly superior anti-anorexia nervosa agents and anti-aggressive agents as well as beta-stimulating agents and antidepressant agents In the following specification, fluorophenacylamine derivatives are understood to mean not only compounds having a fluorophenacyl group or formula $F-C_6H_4-CO-CH_2-$, but also a $\beta$-hydroxyfluorophenethyl group of formula $F-C_6H_4-CHOH-CH_2-$, which derives from the preceding one by reduction of the carbonyl function into alcohol function.

Compounds of the 2-amino-1-(halogenophenyl)-1-ethanol type are included in the formula of French patent No. 1 503 517 and presented as antidiuretic agents. However, it should be noted that this French patent describes no 1-(fluorophenyl), 1-(chlorophenyl), 1-(bromophenyl) and 1-(iodophenyl) derivatives, nor does it suggest their potential actions on the CNS.

It is known that fluorophenacyl-amine derivatives belonging to the family of 2-amino-1-(fluorophenyl)-1-ethanols have already been described. In particular, the article by A.M. Lands, J. Pharmacol. Exptl. Therap. 106, 440-443 (1952) discloses 1-(3-fluorophenyl)-2-isopropylamino-1-ethanol and 1-(3-fluorophenyl)-2-tertiary-butylamino-1-ethanol as being weak pressor agents. The article by L. Villa, et al., Il Farmaco Ed. Scientifica, 24 (No. 3), 329-340 (1969), discloses 1-(4-fluoropyhenyl)-2-isopropylamino-1-ethanol and 1-(2-fluorophenyl)-2-isopropylamino-1-ethanol. These known fluorinated products act on the CNS but they have no, or only slight, aggression-reducing effect. Further, analogous compounds are also disclosed as being adrenergic blocking agents in the article by B. Levy, et al., J. Pharamacol. Exptl. Therap., 133, 202-210 (1961); as appetite-supressing agents in U.S. Pat. Nos. 3,313,687 (Siemer) and 3,465,039 (Seimer); as CNS-stimulant and antidepressant agents in U.S. Pat. No. 3,819,706 (Mehtay) and as anti-diuretic agents in British Patent No. 1,043,510.

It has been unexpectedly found that the new fluorophenacyl-amine derivatives of the present invention, which act on the CNS, have particularly advantageous antiaggressive and anti-anorexia nervosa properties from the therapeutical standpoint.

According to the invention, a compound belonging to the family of fluorophenacyl-amine derivatives of formula:

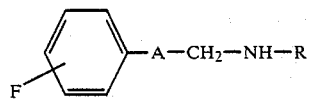

(I)

wherein A is CO or CHOH, and R is $CH(CH_3)_2$ or $C(CH_3)_3$, is recommended as new industrial product, particularly useful in therapeutics, said compound being characterized in that it is selected from the group consisting of N-(4-fluorophenacyl)-isopropylamine, N-(2-fluorophenacyl)-tertiary-butylamino, 1-(2-fluorophenyl)-2-tertiary-butylamino-1-ethanol, 1-(4-fluorophenyl)-2-tertiary-butylamino-1-ethanol, and their addition salts.

From these products, the preferred compounds from the therapeutical standpoint are N-(4-flurophenacyl)isopropylamine and its salts, particularly the hydrochloride.

Addition salts are understood here to mean the acid addition salts obtained by reacting a free base of formula I with an inorganic or organic acid, and the ammonium salts. Among the acids which may be used for salifying the bases of formula I, the following may be particularly mentioned: hydrochloric, hydrobromic, nitric, sulphuric, acetic, propionic, oxalic, fumaric, maleic, succinic, benzoic, cinnamic, mandelic, citric, malic, lactic, tartaric, p-toluenesulphonic and methanesulphonic acids. Among the compounds enabling ammonium salts to be obtained, particular mention may be made of $ICH_3$ and $ClCH_3$. The acid addition salts are the preferred salts, and, among the latter, the most advantageous are the hydrochlorides.

The fluorophenacyl-amine derivatives of this invention may be prepared according to a method known per se, by application of conventional reactional mechanisms. The recommended process for preparation consists of the following:

(1) in obtaining a "carbonyl" compound (A =CO) by reacting a fluorophenacyl halide of formula

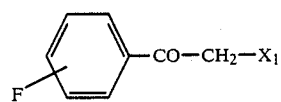

(II)

(wherein $X_1$ is Cl or Br) with an amine of formula

 $H_2NR$ (III)

(wherein R is defined as hereinabove), under reflux for at least 1 hour in an alcohol, preferably methanol, then (2) if necessary, in obtaining an "alcohol" compound (A=CHOH) by reducing the corresponding carbonyl derivative, in particular with $NaBH_4$.

The compounds according to the invention are all active on the CNS and also have interesting cardiovascular effects. In particular, they act on the CNS as sedative agents, antidepressants and superior antiaggressive agents and are unexpectedly indicated in the treatment of anorexia nervosa as well as depression.

DETAILED DESCRIPTION

According to the invention, a therapeutic composition is recommended, particularly useful in the treatment of aggression, anorexia nervosa and depression, characterized in that it contains, in association with a physiogically acceptable excipient, at least one fluorophenacyl-amine derivative according to the present invention or one of its nontoxic addition salts, the active ingredient being, of course, administered at a pharmaceutically effective amount.

Comparative tests have been carried out to demonstrate those effects on animals which distinguish the products according to the present invention from their closest known fluorinated analogues. Among these tests, those concerning the antiaggressive properties and antianorexia nervosa properties have been summarized. More particularly, the reduction of the intergroup aggressiveness was assessed according to the following technique: after 3 week's residence on either side of an opaque partition separating their cage at the center, groups of 3 male mice each weighing about 20g receive by interperitoneal route the products to be tested, in solution in distilled water, the control animals receiving only distilled water by I. P. route. Half an hour later, the two groups of the same cage are brought together by withdrawing the partition and the number of fights which take place in 10 minutes is noted. 3 cages are used for each product to be tested and 6 cages for the control batch not receiving the products to be tested.

The results of Table I hereinafter give the reduction in intergroup aggressiveness with respect to the control batch, all the products to be tested being administered at the dose of 8 mg/kg by I.P. route. These results show (i) that the product according to the invention (Examples 1 to 5) have a clearly greater antiaggressive effect than that of their known analogues (CPI to CP4) and (ii) that there is no structure-activity relationship.

3,819,706 (Mehta). However, a recently published clinical assay by F. Lang, et al. appearing in Societe Medico-Psychologique-Meeting of Monday 4th July, 1983, shows that the compound of Example 3 of the present invention (Code No. CRL 40827) is a beta-stimulant and antidepressant agent which exhibits an unexpected action against anorexia nervosa. Accordingly, comparative tests were carried out to demonstrate this effect and to distinguish the compounds of to the present invention from the closest prior art compounds. These tests were concerned with the determination of weight variation after treatment in animal and in female human patients suffering from anorexia nervosa.

The first series of experiments assessed the weight variation of adult female rats (weighing approximately 190 g each) receiving a daily dose of from 3 to 10 mg/kg of the compound to be tested (batch of 10 animals per product) with respect to control animals (batch of 15 animals). After three weeks of treatment with the compounds hereinafter listed in Table II, the results are summarized in Table III and are expressed as weight variation percentages. In these tables the compounds of the present invention are referenced as Ex 1-Ex 5, and the comparative compounds of the prior art are referenced CP 1-CP 14.

It was expected that all tested compounds should exhibit an appetite depressing action expressed as a negative weight variation after treatment. The results show that surprisingly Ex 3 (CRL 40827) and Ex 5 (CRL 40854) as well as CP 1-2 and CP 4 cannot be considered as appetite supressing substances. Unlike the other compounds which reduce the animal weight by more than 10%, these compounds resulted in a positive weight variation.

TABLE I

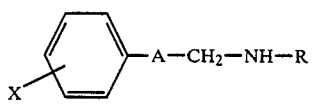

| Product | Code No. | X | A | R | Dose mg/kg | reduction of intergroup aggressiveness |
|---|---|---|---|---|---|---|
| Example 1 (a) | CRL 40727 | 4-F | CO | CH(CH$_3$)$_2$ | 8 | 75% |
| Example 2 (a) | CRL 40828 | 2-F | CO | C(CH$_3$)$_3$ | 8 | 61% |
| Example 3 (a) | CRL 40827 | 2-F | CHOH | C(CH$_3$)$_3$ | 8 | 76% |
| Example 4 (b) | CRL 40827A | 2-F | CHOH | C(CH$_3$)$_3$ | 8 | 78% |
| Example 5 (a) | CRL 40854 | 4-F | CHOH | C(CH$_3$)$_3$ | 8 | 69% |
| CP1 (a) (c) | — | 3-F | CHOH | CH(CH$_3$)$_2$ | 8 | 5% |
| CP2 (a) (c) | — | 3-F | CHOH | C(CH$_3$)$_3$ | 8 | 31% |
| CP3 (a) (d) | CRL 40853 | 4-F | CHOH | CH(CH$_3$)$_2$ | 8 | 40% |
| CP4 (a) (d) | — | 2-F | CHOH | CH(CH$_3$)$_2$ | 8 | 6% |

Notes
(a): hydrochloride;
(b): fumarate;
(c): described by A. M. LANDS;
(d): described by L. VILLA et al.

It was surprisingly discovered that compounds according to the present invention exhibit an unexpected and valuable action against anorexia nervosa. It was generally thought in the prior art that CNS-active substances which exhibit beta-stimulant and antidepressant properties would also exhibit an anorexigenic or appetite-supressant effect. See, for example, U.S. Patents Nos. 3,313,687 (Siemer), 3,465,039 (Siemer), and

TABLE II

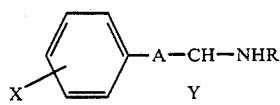

| Product | Code number | X | Y | A | R |
|---|---|---|---|---|---|
| Ex 1 (a) | CRL 40 727 | 4-F | H | CO | CH(CH₃)₂ |
| Ex 2 (a) | CRL 40 828 | 2-F | H | CO | C(CH₃)₃ |
| Ex 3 (a) | CRL 40 827 | 2-F | H | CHOH | C(CH₃)₃ |
| Ex 4 (b) | CRL 40 827A | 2-F | H | CHOH | C(CH₃)₃ |
| Ex 5 (a) | CRL 40 854 | 4-F | H | CHOH | C(CH₃)₃ |
| CP 1(a)(c) | — | 3-F | H | CHOH | CH(CH₃)₂ |
| CP 2(a)(c) | — | 3-F | H | CHOH | C(CH₃)₃ |
| CP 3(a)(d) | CRL 40 853 | 4-F | H | CHOH | CH(CH₃)₂ |
| CP 4(a)(d) | — | 2-F | H | CHOH | CH(CH₃)₂ |
| CP 5(a)(e) | — | 3-F | CH₃ | CO | C(CH₃)₃ |
| CP 6(a)(f) | — | 3-F | CH₃ | CO | CH(CH₃)₂ |
| CP 7(a)(g) | — | 3-F | CH₃ | CHOH | C(CH₃)₃ |
| CP 8(a)(h) | — | 3-F | CH₃ | CHOH | CH(CH₃)₂ |
| CP 9(a)(f) | — | 3-F | H | CO | C(CH₃)₃ |
| CP 10(a)(i) | — | 4-Cl | CH₃ | CO | CH₂CH₃ |
| CP 11(a)(j) | — | H | H | CHOH | C(CH₃)₃ |
| CP 12(a)(j) | — | 3-OH | H | CHOH | CH(CH₃)₂ |
| CP 13(a)(k) | — | 2-Cl | H | CHOH | C(CH₃)₃ |
| CP 14(a)(k) | — | 4-Cl | H | CHOH | C(CH₃)₃ |

Notes:
(a): hydrochloride;
(b): fumarate;
(c): disclosed by A. M. LANDS;
(d): disclosed by L. VILLA et al., Il Farmaco Ed. Scientifica, 24 (N° 3), 329-340 (1969)
(e): disclosed by MEHTA
(f): isomer of Ex 2 suggested by MEHTA
(g): disclosed as intermediate product in published Danish pat. appl. No 134 984;
(h): isomer of Ex 3 suggested by MEHTA
(i): disclosed by SIEMER
(j): laevoisomer disclosed in Brit. patent No 1,043,510(*) suggested by WOLL-WEBER
(*) and in U.S. Pat. No. 3,344,188 (WOLLWEBER)

TABLE III
WEIGHT VARIATION OF ADULT FEMALE RATS

| Product | Code No | dose | weight variation % (a) |
|---|---|---|---|
| Ex 1 | CRL 40 727 | 10 mg/kg | −10.1 (b) |
| Ex 2 | CRL 40 828 | 5 mg/kg | −12.2 (b) |
| Ex 3 | CRL 40 827 | 5 mg/kg | +0.2 |
| Ex 4 | CRL 40 827A | 5 mg/kg | −0.1 |
| Ex 5 | CRL 40 854 | 5 mg/kg | +0.3 |
| CP 1 | — | 5 mg/kg | −0.1 |
| CP 2 | — | 10 mg/kg | +0.3 |
| CP 3 | CRL 40 853 | 5 mg/kg | −10.5 (b) |
| CO 4 | — | 5 mg/kg | −1.4 |
| CP 5 | — | 10 mg/kg | −15.3 (b) |
| CP 6 | — | 10 mg/kg | −16.4 (b) |
| CP 7 | — | 5 mg/kg | −17.3 (b) |
| CP 8 | — | 10 mg/kg | −14.2 (b) |
| CP 9 | — | 10 mg/kg | −10.3 (b) |
| CP 10 | — | 5 mg/kg | −18.1 (b) |
| CP 11 | — | 10 mg/kg | −8.5 |
| CP 12 | — | 5 mg/kg | −7.3 (b) |
| CP 13 | — | 5 mg/kg | −15.4 (b) |
| CP 14 | — | 5 mg/kg | −13.2 (b) |

Note
(a) with respect to the control animals
(b) statistically significant

In a second series of experiments women suffering from anorexia nervosa were treated with Ex 3, Ex 5, CP1, CP2 and CP4 to determine which products would induce weight uptake. Those compounds which induce the expected prior art weight reduction were not utilized in this series of tests to avoid the ethical problem that may have resulted from administering potential appetitedepressing agents to anorexia nervosa subjects. The results of this series of experiments are summarized hereinafter in Table IV. In conjunction with a normal diet, patients were given either a placebo (Treatment A), or one of the compounds to be tested (Treatments B-F) at a daily dose of 3 mg per os (more precisely, one tablet at breakfast time and one tablet at dinner time, each tablet containing 1.5 mg of compound to be tested) for 30 days. These results show that Ex 3 (which produces a weight variation of +4.3 to +14.1 kg) and Ex 5 (which produces a weight variation of +4.1 to +10 kg) confirm the results obtained by F. Lang, et al. and demonstrate the effectiveness of these products as antianorexia nervosa compounds.

TABLE IV
CLINICAL RESULTS

| Patient | age year | ideal weight kg (a) | weight before treatment kg | treatment (b) | weight variation after treatment kg |
|---|---|---|---|---|---|
| 1 | 18½ | 47 | 32.3 | A | +0.1 |
| 2 | 19 | 50 | 37.6 | A | −0.2 |
| 3 | 24 | 50 | 36 | A | −0.2 |
| 4 | 16½ | 49 | 31.5 | A | +0.1 |
| 5 | 16½ | 45 | 29.7 | A | (c) |
| 6 | 19 | 50 | 31.4 | A | +0.1 |
| 7 | 23 | 48 | 30.3 | A | −0.1 |
| 8 | 31 | 45 | 28.9 | A | +0.1 |
| 11 | 25 | 48 | 31.5 | B | +11.1 |
| 12 | 19½ | 50 | 30.6 | B | +12.6 |
| 13 | 16½ | 52 | 32 | B | +4.5 |
| 14 | 15½ | 48 | 32.6 | B | +7.2 |
| 15 | 20 | 49 | 31.5 | B | +8.1 |
| 16 | 20½ | 49 | 33.4 | B | +4.3 |
| 17 | 20 | 50 | 35 | B | +5 |
| 18 | 21 | 46 | 29.7 | B | +14.1 |
| 19 | 18 | 51 | 31 | B | +7.3 |
| 20 | 32 | 45 | 29.3 | B | +10.7 |
| 21 | 21 | 46 | 30.5 | C | +4.5 |
| 22 | 19½ | 50 | 32 | C | +7.8 |
| 23 | 17 | 52 | 35 | C | +10 |
| 24 | 28 | 46 | 29.5 | C | +4.1 |
| 25 | 18½ | 49 | 30.5 | C | +7.5 |
| 31 | 19 | 48 | 31 | D | +0.2 |
| 32 | 19½ | 48 | 33 | D | −0.2 |
| 33 | 27 | 45 | 30.8 | D | (c) |
| 34 | 18 | 50 | 29.4 | D | (c) |
| 35 | 16½ | 48 | 30.5 | D | +0.1 |
| 41 | 24½ | 48 | 31 | E | −0.1 |
| 42 | 19 | 48 | 32.3 | E | −0.3 |
| 43 | 18½ | 49 | 29.5 | E | +0.1 |
| 44 | 29 | 45 | 31.2 | E | −0.2 |
| 45 | 21 | 50 | 32.5 | E | −0.1 |
| 51 | 22 | 45 | 31.8 | F | 0 |
| 52 | 27 | 47 | 30.5 | F | (c) |
| 53 | 21 | 45 | 29.8 | F | −0.3 |
| 54 | 19 | 45 | 32.1 | F | +0.2 |
| 55 | 17½ | 50 | 31.2 | F | −0.1 |

Notes
(a) in view of patient age and height
(b) nature of treatment:
A placebo for 30 days
B daily dose of 3 mg of Ex 3 for 30 days
C daily dose of 3 mg of Ex 5 for 30 days
D daily dose of 3 mg of CP 1 for 30 days
E daily dose of 3 mg of CP 2 for 30 days
F daily dose of 3 mg of CP 4 for 30 days
(c) treatment stopped since untolerated Some examples of preparation have been given hereinafter by way of non-limiting illustration.

Preparation I

Obtaining of the hydrochloride of N-(4-fluorophenacyl)-isopropylamine

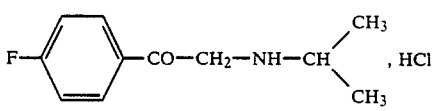

(Example 1: Code No.: CRL 40727)

25 ml of bromine are poured, dropwise, into a solution, cooled by an ice bath, of 69 g(0.5 mol) of parafluoroacetophenone in 100 ml of acetic acid. The mixture is stirred for one hour and evaporated to dryness. The residue is taken up in 100 ml of methanol and the solution thus obtained is poured in a solution of 210 ml of isopropylamine in 100 ml of methanol. It is refluxed for 2 hours, and evaporated to dryness. The residue is taken up in water, the free base of the expected product is extracted with ethyl acetate, the solvent is dried and the hydrochloride is precipitated by hydrochloric ethanol. By recrystallisation in an acetone-methanol (1:1) v/v mixture, 17.2 g (yield: 14.8%) of CRL 40727 are obtained. m.p. 207° C. (with decomposition).

Analysis % N measured=6.01%.
% N theoretical=6.04%.

Preparation II

Obtaining of the hydrochloride of N-(2-fluorophenacyl)-tertiary-butylamine

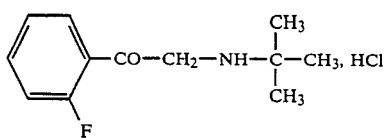

(Example 2; Code No.: CRL 40828)

50g (0.362 mol) of orthofluoroacetophenone are dissolved in 75 ml of acetic acid. The mixture is cooled by an ice bath and 18.1 ml of bromine are poured dorpwise. It is left in contact for 1 hour, evaporated to dryness and the residue is taken up in 100 ml of methanol. The solution thus obtained is poured into a solution of 132 g of tertiary-butylamine in 100 ml of methanol. It is refluxed for 1 hour, evaporated to dryness, the residue is taken up in water, extracted with ether and the expected hydrochloride is precipitated by hydrochloric ethanol. By recrystallisation in an acetone-ethanol (1:1) v/v mixture, 18 g (yield =20%) of CRL 40828 are obtained. m.p. =240° C. (with decomposition).

Analysis: % N measured=5.74%.
% N theoretical=5.7%.

Preparation III

Obtaining of the hydrochloride of 1-(2-fluorophenyl)-2-teritary-butylamine-1-ethanol.

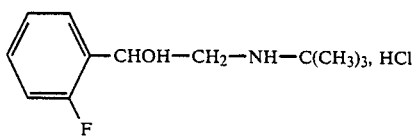

(Example 3; Code No.: CRL 40827)

0.04 mol of N-(2-fluorophenacyl)-tertiary-butylamine (free base of the CRL 40828) is dissolved in 120 ml of methanol. Cooling is effected to −5° C. and 3 g of sodium borohydride are added. It is left in contact for 1 hour. The excess NaBH4 remaining in the reaction medium is destroyed by means of 5 ml of acetic acid, then the mixture is evaporated to dryness. The residue of evaporation is taken up in water, the pH is adjusted to 11 by means of NaOH, extracted with ether, the ethereal phase is washed with water and said ethereal phase is dried over MgSO4. After filtration, the free base is collected then the expected hydrochloride is precipitated by means of hydrochloric ethanol. By recrystallization in an acetone-ethanol (1:1) v/v mixture, 8 g (yield: 80%) of CRL 40827 are obtained. m.p. =180.5° C.

Analysis: % N measured=5.60%.
% N theoretical=5.65%.

Preparation IV

Obtaining of the fumarate of 1-(2-fluorophenyl)-2-tertiary-butylamino-1-ethanol (Example 4; Code No. CRL 40827 A)

By reacting 1-(2-fluorophenyl)-2-tertiary-butylamino-1-ethanol (free base obtained in Preparation III) with fumaric acid, CRL 40827A is obtained. m.p. 195°-200° C. (with decomposition).

Preparation V

Obtaining of the hydrochloride of 1-(4-fluorophenyl)-2-tertiary-butylamino-1-ethanol

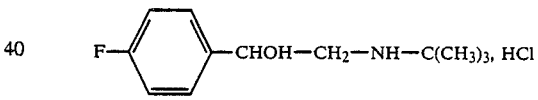

(Example 5: Code No.: CRL 40854)

50 g (0.289 mol) of α-chloro-p-fluoroacetophenone are dissolved in 900 ml of methanol. The mixture is cooled to −5° C. and 5.80 g of NaBH4 are added. It is left in contact for 1 hour then 10 ml of acetic acid are added. 151 ml of tertiary-butylamine are added and the mixture is refluxed for 12 hours. It is evaporated to dryness and the residue of evaporation is taken up in distilled water. The free base which has crystallised is filtered off and, by recrystallisation in hexane, 39 g (yield 63%) of 1-(4-fluorophenyl)-2-tertiary-butylamino-1-ethanol are obtained. m.p. 117° C.

This base is dissolved in diethyl ether, the hydrochloride is precipitated by means of hydrochloric ethanol. By filtration and drying in vacuo over P2O5, 44 g (yield: 61%) of CRL 40854 are obtained. m.p. 176° C.

CRL 40854 may also be prepared according to the process of preparation III, when replacing the N-(2-fluorophenacyl)-tertiary-butylamine by N-(4-fluorophenacyl)-tertiary-butylamine.

Additional tests carried out with the preferred products according to the present invention have been summarized hereinafter.

(A) Tests relative to CRL 40727 (Example 1)

1. Toxicity

The maximum non-lethal dose, LD-O, is greater than 128 mg/kg and less than 256 mg/kg, in the mouse, by I.P. route.

2. Action on the CNS

CRL 40727 has a certain number of sedative-type effects, namely:

sedation and hyporeactivity in the mouse,
hypomotility and reduction of aggressiveness in the mouse,
hyopthermia and potentiation of the hypothermiainducing effects of apomorphine, oxotremorine and reserpine,
moderate antagonism of the stereotypies induced by amphetamine.

3. Action on the cardiovascular system

(a) By the intraveinous route

Two dogs receive CRL 40727 by the intraveinous route, in perfusion in 6 minutes, at the successive doses of 0.1 mg/kg, 1 mg/kg, 2.5 mg/kg/ 5 mg/kg, 10 mg/kg and 20 mg/kg. Their arterial pressure, cardiac frequency, flow rate of the femoral artery and rectal temperature are measured.

The following is observed.

CRL 40727 increases the flow rate of the femoral artery from the dose of 1 mg/kg; the effect increases with the dose, up to 10 mg/kg, dose for which +140% is attained.

From 5 mg/kg, the differential arterial pressure increases; the diastolic and average arterial pressures reduce from 10 and 20 mg/kg respectively.

The cardiac frequency is not clearly modified.

The skin becomes pink from 2.5 to 10 mg/kg.

The bilary liquid remains yellow; the rectal temperature is not modified.

Tachycardia induced by isoprenaline is reduced, the cardiac frequency passes on average to 182 beats/min after 10 mg/kg, whilst it was 215 beats/min in the control; hypotension is not modified.

A complementary experiment was undertaken; one dog receives an additional dose of 40 mg/kg I.V. of CRL 40727, and a greater hypotension is observed than at the preceding dose, the bilary liquid remaining yellow; a second dog receives a reference product, the hydrochloride of (2, 4, 6-trimethoxyphenyl)-3-pyrrolidinopropyl)-ketone—which is described in British Patent No. 1,325,192, is coded LL 1656 and is marketed under the name FONZYLANE—at the dose of 6 mg/kg I.V. and it is observed that the rate of flow of the femoral artery does not increase more with LL1656 than with the dose of 10 mg/kg of CRL 40727.

(b) By the intraduodenal route

Three dogs receive CRL 40727 by the intraduodenal route at the successive doses of 1 mg/kg, 2.5 mg/kg, and 10 mg/kg. The same parameters as hereinabove are measured. The following is observed.

CRL 40727 clearly increases the rate of flow of the femoral artery from the dose of 2.5 to 5 mg/kg; the effect increases only slightly with the dose. From 10 mg/kg, a hypotensive action is manifested. The skin becomes very slightly pink from 2.5 mg/kg.

The biliary liquid remains yellow. The rectal temperature is not modified.

Tachycardia induced by isoprenaline is reduced. The cardiac frequency passes on average to 165 beats/min after 10 mg/kg of CRL 40727, whilst it reached 220 beats/min in the control. Hypotension is not modified.

Complementary tests were undertaken; one dog receives an additional dose of 20 mg/kg by I.D. route. A greater hypotensive action is observed, without additional vasodilator effect. The same result is obtained on another dog in which are injected 5 mg/kg I.V. of CRL 40727 at the end of the test. moreover, the LL 1656 injected thereafter by the intraveinous route, at the dose of 6 mg/kg, does not cause additional vasodilation.

In conclusion, the results obtained by the intraveinous route and by the intraduodenal route are difficult to compare, hypotension occurring in the dogs treated by the intraveinous route only from 20 mg/kg, whilst it appears with the same intensity in the dogs treated by the intraduodenal route at 10 mg/kg.

The vasodilator action of CRL 40727 is perhaps due to a $\beta+/2$ action; no $\beta+/1$ action is observed (no tachycardia), no bradycardia; on the contrary, the tachycardia-inducing action of isoproterenol is reduced. Moreover, it will be noted that the biliary liquid remains yellow, even after the accumulated dose of 38.5 mg/kg I.V.

(B) Tests relative to CRL 40827 (Example 3)

CRL 40827, in solution in distilled water, was administered by the intraperitoneal route in a volume of 20 ml/kg in the male mouse and a volume of 5 ml/kg in the male rat.

1. Toxicity

The maximum non-lethal dose, LD-O, is greater than 64 mg/kg and less than 128 mg/kg in the male mouse.

2. Action on the CNS

Interaction with apomorphine

(a) Mouse

Batches of 6 mice receive CRL 40827 half an hour before the subcutaneous injection of apomorphine at the does of 1 or 16 mg/kg. It is observed that, at doses of 0.5 mg/kg and 2 mg/kg and especially 8 and 32 mg/kg, CRL 40727 clearly opposes the hypothermia-inducing action of the strong dose of apomorphine but does not modify the behaviour of verticalisation and the stereotypies.

(b) Rat

CRL 40827 is administered to batches of 6 rats half an hour before subcutaneous injection of 0.5 mg/kg of apomorphine. It is observed that CRL 40827 does not modify the stereotypies induced by apomorphine in the rat.

Interaction with amphetamine

Amphetamine (2 mg/kg) is injected by the intraperiotoneal route to batches of 6 rats, half an hour before administration of CRL 40827. It is noted that, except for the isolated reduction of the index of stereotypies, observed at the dose of 4 mg/kg, CRL 40827 does not modify stereotypies induced by amphetamine.

Interaction with reserpine

Four hours after the intraperitoneal injection of 2.5 mg/kg of reserpine, batches of 6 mice receive the CRL 40827. It is observed that, from the dose of 0.5 mg/kg, CRL 40827 clearly fights hypothermia induced by reserpine without modifying the ptosis.

Interaction with oxotremorine

CRL 40827 is administered to batches of 6 mice half an hour before the intraperitoneal injection of 0.5 mg/kg of oxotremorine. It is observed that, from a dose of 0.5 mg/kg upwards, CRL 40827 antagonises the hypothermia-inducing action of oxotremorine; this effect is very clear at 32 mg/kg. Moreover, CRL 40827 does not modify the intensity of the tremors provoked by oxotremorine. Finally, CRL 40827 does not modify the signs of cholinergic peripheral stimulation which appear after administration of oxotremorine.

Action on the four plate test, traction and electric shock

The test is made on batches of 10 mice, half an hour after the administration of CRL 40827. CRL 40827 does not cause increase in the number of incorrect moves which are punished; it does not bring about any major motor incapacity and, at a high does, opposes the convulsing effects of the electric shock.

Action on the spontaneous motility

Half an hour after having received CRL 40827, the mice (6 per dose, 12 controls) are placed in an actimeter where their motility is recorded for 30 minutes. It is observed that CRL 40827 virtually does not modify the spontaneous motor activity of the mouse.

Action with respect to some behaviour disturbed by various agents (a) Motility reduced by habituation to the cage After remaining 18 hours in the actimeters, the mice (6 per dose, 12 controls) receive CRL 40827. They are immediately replaced in their respective cages and, half an hour later, their motility is recorded for 30 minutes. At a high dose (34 Mg/kg), CRL 40827 seems to provide a moderate renewal of motor activity.

(b) Motility reduced by hypoxic aggression

Half an hour after having received the CRL 40827, the mice (10 per dose, 20 controls) are subjected to acute anoxia by pressure reduction [depression of 600 mm Hg (i.e. $8 \times 10^4$ pascals) in 90 seconds, return to normal pressure in 45 seconds], then they are placed in an actimeter where their motility is recorded for 10 minutes. It is noted that CRL 40827 does not produce any improvement in the motor recovery of mice whose motility has been reduced due to a brief stay in a cage under reduced pressure.

(c) Asphyxic anoxia

Batches of 10 mice receive CRL 40827 half an hour before the intraperitoneal administration of 34 mg/kg of Gallamine Triiodoethylate. At the highest dose (34 mg/kg CRL 40827 prevents the appearance of convulsions and death in 40% of the animals.

Conclusion relative to the action on the CNS

The antagonism of the hypothermiae induced by apomorphine, reserpine or oxotremorine makes it possible to foresee an activity of antidepressant type for the CRL 40827. These antagonisms being observed in the absence of anticholinergic effect, the CRL 40827 therefore differs from the imipraminic antidepressants.

On the other hand, the absence of antagonism of the ptosis induced by reserpine, and of motor stimulation with stereotypies makes it possible to distinguish the CRL 40827 from the IMAO and amphetaminic compounds respectively. In brief, there is a strong presumption that the CRL 40827 behaves like the adrenergic stimulants.

Furthermore, CRL 40827 exerts solely anticonvulsive effects at a high dose. Finally, it reduces the inter-group aggressiveness in the mouse.

3. Action on the cardiovascular and respiratory system

It is observed that CRL 40827 acts as hypotensive and tachycardiainducing agents in the anaesthetized dog and in the genetically hypotensive, awake rat, that it reduces the vascular resistances of the territories explored (vertebral, femoral and renal) and the total peripheral resistance, that it reduces the work of the left-hand ventricule and shortens the diastole, that it stimulates respiration, that it reduces the hypertensive effects of the noradrenaline from the dose of 1 mg/kg in the dog (the maximum effect being attained at the dose of about 10 mg/kg).

The local rates of flow of blood do not increase, but the resistances diminish; this phenomenon would imply that the CRL 40827 induces an arterial peripheral vasodilation at the same time as an increase in the veinous drainage since the cardiac output remains equal.

4. Action on the biliary secretion

In the dog anaesthetized with Nembutal, the normal biliary output collected in 30 minutes is 1.5 ml; the biliary output increases after intraduodenal injection of CRL 40827 and passes to 1.75 ml for 2.5 mg/kg of CRL 40827, to 2.25 ml for 5 mg/kg and to 2.5 ml for 10 mg/kg. In the rat anaesthetized with Nembutal, the biliary output increases 1 to 3 hours after I.V. injection of CRL 40827 at the doses of 5 mg/kg and 25 mg/kg.

5. Local anaesthetic effect

The anaesthetic effect was studied in the guinea pig after injection of CRL 40827 by the intradermic route in a volume of 0.2 ml at concentrations of 0.1, 0.5 and 1% (3 guinea pigs per dose). Each animal receives physiologcal serum, procaine and CRL 40827 in defined zones.

The test, which consists in a series of 6 injections in the injected zone is carried out 5, 10, 15, 20, 25 and 30 minutes after the injection. It is ascertained that the CRL 40827 has a local anesthetic effect when it is administered at concentrations of 0.5 and 1%.

(C) Tests relative to CRL 40854 (Example 5)

CRL 40854, in solution in distilled water, was administered by the intraperiotoneal route in a volume of 20 ml/kg in the male mouse and 5 ml/kg in the male rat.

1. Toxicity

The maximum non-lethal dose, LD-O, is greater than 128 mg/kg and less than 256 mg/kg in the mouse.

2. Action on the CNS

By proceeding according to the modi operandi given hereinabove, for the CRL 40827, the following is observed.

Interaction with apomorphine

At the doses of 16 and 64 mg/kg in the mouse, CRL 40854 moderately opposes the hypothermia-inducing action of apomorphine without modifying the behaviour of verticalisation and stereotypies.

In the rat, the CRl 40854 does not modify the stereotypies induced by apomorphine.

Interaction with amphetamine

At the doses of 8 and 32 mg/kg, CRL 40854 potentialises the duration of the stereotypies induced by amphetamine.

Interaction with reserpine

At the doses of 4, 16 and 64 mg/kg, CRL 40854 moderately antagonises the hypothermia induced by reserpine without modifying the ptosis.

Interaction with oxotremorine

At the doses of 16 and 64 mg/kg, CRL 40854 aggravates the hypothermia-inducing effect of oxotremorine. It does not modify the tremours and signs of cholinergic peripheral stimulation.

Action on the four plate test, traction and electric shock

Like the CRL 40827, the CRL 40854 does not produce any increase in the number of incorrect moves which are punished and does not bring about any major motor incapacity. On the other hand, it does not modify the convulsing effects of the electric shock.

Action on the spontaneous motility

At a high dose (64 mg/kg), the CRL 40854 moderately reduces the spontaneous motility of the mouse.

Action with respect to a few behaviour disturbed by various agents (a) Motility reduced by habituation to the cage The CRL 40854 does not provoke a clear renewal of the motor activity in the mouse habituated to its cage.

(b) Motility reduced by hypoxic aggression

Like the CRL 40827, the CRL 40854 does not produce any improvement in the motor recovery in the mouse.

(c) Asphyxic anoxia

The CRL 40854 does not modify the appearance of convulsions and death consecutive to an anoxia provoked by blocking (curarisation).

In conclusion, the CRL 40854, which reduces the intergroup aggressiveness in the mouse, has surprising results with respect to the conventional sedative and antidepressant agents.

In clinic, good results have also been obtained with CRL 40727, CRL 40827 and CRL 40827A, in the psychotropic domain as sedative and antidepressant agents in man after having been administered in the form of tablets or gelatin-coated capsules each containing 5 mg of active ingredient, at the rate of 3 tablets or gelules per day.

The results of several series of clinical trials demonstrating the therapeutic value of CRL 40827 on depression will be given below.

I. First series of clinical trials

It relates to 14 patients with severe depression (Major Affective Disorder of DSM-III), 8 bipolar and 6 unipolar, and to 4 patients displaying neurotic depression. These patients were frequently difficult cases since 7 showed a poor previous response to tricyclic compounds and 4 required shock therapy. All had been admitted to hospital for a recent aggravation of a depressive episode, the start of which was between 15 days and 3 months before admission and on day 1 (inclusion in the study) they had scores of 35 for the MADRS (Montgomery Asberg),
31 for the ERD (Widlocher abatement scale),
6 for the COVI scale (anxiety).

CRL 40827 was studied for 14 days on these patients, at extreme dosages of 1 to 9 mg, with a mean dosage of 3 to 6 mg/24 hours divided into 3 portions.

All of the patients were examined on day 8 (MADRS, ERD, COVI). Twelve were examined on day 14. In fact, 4 patients had left the trial before day 14 because of therapeutic success and 2 because of failure.

The results of the gradings permit the following conclusions:

1. There is a real effiicacy,
2. The onset of the effect is early in bipolar depressives,
3. Unipolar depressives improve partially during the first week and the improvement continues during the second week. "Responders" and "non-responders" seem to exist in this group,
4. Neurotic depressives are not specifically sensitive to the product (this is the case for the "true" antidepressants, the possible favourable response in the case of the latter being linked to sedative properties).

Finally, it is very interesting to note that when the group of 14 patients showing a "Major Affective Disorder" is considered, 10 of the 14 may be regarded as cured after 14 days.

With regard to tolerance, CRL 40827 is completely different from the beta-stimulants currently known, the therapeutic activities of which are peripheral (pneumological and obstetrical):

no significant effect on the blood pressure or the heart rate,
no digestive manifestations,
no significant effect on blood glucose levels.

In conclusion, this first series of clinical trials lets it be said that CRL 40827, in a dosage of 3 to 6 mg per day, is effective in the treatment of severe depressions, particularly bipolar depressions. This efficacy is early (from day 8) and intense (10 out of 14 cured by the 14th day) and is obtained with a tolerance which is completely different from that of peripheral beta-stimulants.

II. Second series of clinical trials

This second series of trials relates to a group of 81 patients (42 males, 39 females), aged from 21 to 82, displaying depressive symptoms within the framework of various pathologies.

72 patients were treated with the mean dose of 3 mg/24 hours (between 1 and 4 mg/24 hours). They exhibited

--- manic-depressive psychosis and

| | |
|---|---|
| melancholia | 6 cases |
| isolated depressive attack | 5 cases |
| alcoholism | 12 cases |
| neurosis | 8 cases |
| psychosis | 32 cases |
| others* | 9 cases |

*"others" signifies: hypochondria, mental anorexia.

9 patients were treated with a dosage of 6 mg/24 hours and exhibited:

| | |
|---|---|
| melancholia | 1 case |
| plain depressive attack | 3 cases |
| other pathological type* | 5 cases |

The mean duration of treatment was from 3 to 4 months with a maximum of patients (32) treated for between 15 days and 2 months.

The results may be considered as good in more than 60% of the cases with a good tolerance to the daily dosages of 3 to 4.5 mg/24 hours. The use of a higher dosage (6 mg/24 hours) does not appear to improve the results and is responsible for certain side-effects which disappear when the dosage is reduced.

III. Third series of clinical trials Population

The study was carried out on 12 patients aged from 25 to 61 (6 males, 6 females), all of whom had been hospitalized.

They satisfied the criteria for a major depressive episode in the DSM-III classification, being in summary:
Pronounced and/or persistent depressive state,
Four symptoms for at least two weeks:
  anorexic loss in weight or hyperphagia/gain in weight,
  insomnia or hypersomnia,
  agitation or slowing down,
  loss of pleasure and of interest,
  loss of energy,
  discredit,
  slowed down thought process, indecision,
  suicidal tendencies,
No signs of delirium or bizarre behaviour prior to the start of the depressive episode.
The following criteria for exclusion were respected:
  women who were pregnant or not using contraceptives,
  ischaemia or myocardial excitability,
  severe arterial hypertension,
  diabetes,
  epilepsy,
  associated alcoholism,
  treatment with Esperal,
  any other severe somatic pathology.

Prescription

The trial period was preceded if necessary by a "wash-out" of antidepressants or neuroleptic agents.

Treatment with benzodiazepine or placebo was carried out from day −7 to day 0.

The trial proper comprised two periods:
from day 0 to day 7: a blind period in which the patient received either 3, 4, 5 or 6 mg of CRL 40827
from day 8 to day 21: an open period starting with a dose equal to that of the blind period and subsequently adapting it if necessary.

The product was administered in the morning as a single dose of 2 tablets.

The only other drugs prescribed were benzodiazepines, mainly Lorazepam.

In certain cases the trial was extended for up to several weeks.

Evaluation

Study of the psychotropic effects

Three scales indicating the intensity of the depression were used:
  MADRS of Montgomery and Asberg,
  the 17-item Hamilton depression scale,
  the Widlocher depressive abatement scale.
The evaluations carried out were:
  essentially on days 0, 7 and 21,
  where required, on days −7, 4, 14 and later than
A single practitioner carried out all of the evaluations (more than 130).

Compilation of data

Record form

The clinical data were entered in a record form comprising:
  identification data,
  case histories,
  recent events in patient's life,
  the history of the current episode,
  the semiology,
  the detailed DSM-III diagnosis for axes I and II,
  the psychometric scales,
  the checklist of side-effects.

Televised recordings

In the case of 11 patients a recording of the interviews was made with video recorders at the start and at the en of the trial and sometimes in the course of the trial.

In total, 28 recordings were made, 24 of which were by the same classifier, and the documents were reviewed to reexamine the development of the patients.

Balanced study

It comprises the remarks made for the population as a whole with respect to
  psychotropic effects,
  side-effects.

Psychometric study

The data taken into account related to the psychometric scores on days -7, 0, 7 and 21.
  They enable:
  the variation in the total score and
  the symptomatic development to be studied.

Variation in the total score

This was assessed during the Wilcoxon T test for paired series comparing the differences in the total score per scale between two times.

The results below express the probability of a significant variation (at 0.05; at 0.01) or not (NS):

|  | MADRS | HDRS | RALT |
|---|---|---|---|
| Day−7/day 0 | NS | NS | NS |
| Day 0/day 7 | 0.05 | NS | NS |
| Day 0/day 21 | 0.01 | 0.05 | 0.05 |

The antidepressant effect is thus significant with the MADRS from day 7, while on day 21 it becomes significant for the two other scales and still more significant for the MADRS.

These results expressed as quantitative data: mean (m), standard deviation (s) are given below:

|  |  | DAY 0 | DAY 7 | DAY 21 |
|---|---|---|---|---|
| MADRS | m | 28.3 | 24.33 | 16.75 |
|  | s | 6.61 | 8.39 | 6.73 |
| HDRS | m | 26.1 | 24.6 | 20 |
|  | s | 7.18 | 8.87 | 5.73 |
| RALT | m | 33 | 30.53 | 25.14 |
|  | s | 7.88 | 9.61 | 11.05 |

If the relative variation is considered expressing as a percentage the difference in the scores between day 0 and day 21 divided by the score on day 0, an improvement of, by decreasing order of magnitude:
. MADRS: 40%
. RALT: 24%
. HDRS: 23%
is found.

Since this calculation neutralizes the differences in degrees between scales, it is the MADRS which is the scale most sensitive to variations.

Symptomatic evolution

The symptomatic effect was examined considering the five items improved most per scale. This ranking was defined by establishing the difference in the total score between day 0 and day 21 for each symptom and for all of the cases. Equal values were divided in the inverse function of the initial score.

MADRS ranking
1 evident melancholy
2 inner tension
3 expressed melancholy
4 lassitude
5 affective anaesthesia HDRS ranking
1 guilt
2 suicide
3 depressive mood
4 work and activity
5 psychic anxiety RALT ranking
1 rumination
2 bearing
3 verbal delivery
4 interest
5 variety of topics It thus appears:
that the most specific signs of the depressive state appear in this list (evident and expressed melancholy, affective anaesthesia, depressive state, interest); THUS, THE IMPROVEMENT IN THE SUBJECTS IS THE RESULT OF AN ANTIDEPRESSANT ACTION.

Taken as a whole, the three series of clinical trials which are described above and relate to 111 *patients* demonstrate that CRL 40827, a central betaagonist, is an effective treatment for severe depression and that this therapeutic efficacy is observed
not only on the conventional international psychometric scales (Hamilton depression; HDRS, Montgomery and Asberg; MADRS, WIDLOCHER depressive abatement scale), the scores of which improve significantly from the 14th day of treatment,
but also in a relevant clinical manner, since some hospitalized patients were able to leave the establishment before the 14th day (first trials) or improved in a spectacular manner under CRL 40827 even though their condition had not been altered with other antidepressant treatments (second series of trials).

The final series of trials presented confirms the uniqueness of the antidepressant therapeutic activity of CRL 40827 since it shows, compared with placebo, under stringent methodological conditions, that this action is very rapid, from the 7th day of treatment, which is completely unique in the category of antidepressants.

IV. Fourth series of clinical trials

CRL 40827 was studied, within the framework of a methodology for clinical screening of psychotropic molecules, on patients recruited according to symptomatic criteria, and evaluated in a double-blind study comparing with placebo, namely using the AMDP system, before and after 7 days of administration.

A first study compared the effect of placebo (n = 24) with that of 3 mg/day (n = 24) of CRL 40827 in patients displaying a pathology for which a renewal of vital energy and a desinhibition was to be obtained, either within the framework of a depression or of a schizophrenic disorder.

The results showed, after verification of the comparability of the groups at day 0, that the dose of 3 mg/day improves more than the placebo, and in a statistically significant manner (ANOVA), the apathy/slowing-down factors and the psycho-organic syndroms of the AMDP system.

In order to increase the size of the groups, a second study was undertaken, in accordance with the findings made at the end of the first.

After verifying the satisfactory homogeneity of the treatment groups and reference groups on day 0, the two trials were "pooled". The sizes were thus brought to 87 patients (43 placebo and 44 treated with 3 mg/day).

Under these conditions, inference analyses (ANOVA) confirmed the improvement, which was statistically significant in favour of CRL 40827, in apathy/slowing down factors and psycho-organic syndroms.

The same analyses applied to the ABATEMENT scale, which was used at the same time, did not enable an effect of CRL 40827 to be shown either at the level of each of the items or at the level of the global rating (with the exception of language and verbal delivery in the second study).

A factorial analysis of change was carried out in order to determine, for the two studies, the profiles of the groups and that of the responders.

After having selected the 36 items for which there was a rating on day 0 and/or day 7 of at least ≧ slight for more than 40% of the patients, principal component analysis for the CRL 40827 cases was carried out.

This descriptive analysis showed, like the conventional analyses, the significant response of patients who had received the placebo. It also showed that a regrouping factor of the items in relation to the inhibition and the thymic disorders improved with CRL 40827. This factor, which represents 22% of the variance, is made up of items very directly related to depression. It is particularly homogeneous and regroups items which show considerable variation:

vital sense disorders,
loss of energy,
asthenia,
melancholy,
affective monotony,
inhibition of energy,
inhibited thought,
reduced sexual desire,
slowed thought process.

Variance analysis, carried out on the items retained for the principal component analysis, permitted the statement that the molecule appears to be mainly active at the thought level (slowed thought—impoverished thought) and the loss of energy level.

In total

Under the experimental conditions, the results have shown that CRL 40827, prescribed in the dosage of 3 mg/day in two doses, leads to psycho-behavioural changes above all linked to an improvement in the classical symptoms linked to the depressive pathology (depressive disorders, apathy/slowing down, loss of energy).

GENERAL CONCLUSION

CRL 40827 is a central beta-agonist for which pharmacological studies show an activity predictive of an antidepressant effect in the conventional tests with a very weak peripheral beta-stimulant, and in particular cardiovascular, activity, which differentiates it entirely from other beta-agonists. It manifests itself early: from day 7 of treatment,
intensely: all of the studies show a significant improvement in the psychometric scores (HDRS, MADRS, abatement) and a pertinent clinical improvement even in the case of resistant depression,
durably: the improvement on day 21 is greater than on day 14 and day 7.

CRL 40827, which exerts this therapeutic activity when taken in a single oral dosage of 3 to 6 mg/24 hours, is thus the only essentially central beta-agonist which is effective in the treatment of depression.

What is claimed is:

1. A process for the treatment of depression comprising administering to a human in need thereof an antidepressant amount of a compound selected from 1-(2-fluorophenyl)-2-tertiary-butylamino-1-ethanol and an addition salt thereof.

2. Process as claimed in claim 1 comprising administering to a human in need thereof an antidepressant amount of hydrochloride of 1-(2-fluorophenyl)-2-tertiarybutylamino-1-ethanol.

* * * * *